(12) United States Patent
Perschbacher et al.

(10) Patent No.: US 7,840,265 B2
(45) Date of Patent: Nov. 23, 2010

(54) ANTI-TACHYARRHYTHMIA SYSTEM WITH SELECTIVELY ACTIVATED DETECTION ENHANCEMENTS

(75) Inventors: David L. Perschbacher, Coon Rapids, MN (US); James O. Gilkerson, Stillwater, MN (US); James Kalgren, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 179 days.

(21) Appl. No.: 12/264,771

(22) Filed: Nov. 4, 2008

(65) Prior Publication Data

US 2009/0157126 A1    Jun. 18, 2009

Related U.S. Application Data

(60) Provisional application No. 61/008,156, filed on Dec. 18, 2007.

(51) Int. Cl.
*A61N 1/00* (2006.01)
(52) U.S. Cl. .......................................... 607/4
(58) Field of Classification Search ............ 607/4, 607/5, 14
See application file for complete search history.

(56) References Cited

U.S. PATENT DOCUMENTS

| | | | |
|---|---|---|---|
| 4,236,524 A | 12/1980 | Powell et al. | |
| 4,562,841 A | 1/1986 | Brockway et al. | |
| 5,107,850 A | 4/1992 | Olive | |
| 5,113,869 A | 5/1992 | Nappholz et al. | |
| 5,292,341 A | 3/1994 | Snell | |
| 5,360,437 A | 11/1994 | Thompson | |
| 5,400,795 A | 3/1995 | Murphy et al. | |
| 5,549,654 A | 8/1996 | Powell | |
| 5,607,460 A | 3/1997 | Kroll et al. | |
| 5,620,471 A | 4/1997 | Duncan | |
| 5,716,382 A | 2/1998 | Snell | |
| 5,716,384 A | 2/1998 | Snell | |
| 5,724,985 A | 3/1998 | Snell et al. | |
| 5,725,559 A | 3/1998 | Alt et al. | |
| 5,755,736 A | 5/1998 | Gillberg et al. | |

(Continued)

FOREIGN PATENT DOCUMENTS

EP    0360412 A1    3/1990

(Continued)

OTHER PUBLICATIONS

"U.S. Appl. No. 09/569,928, Notice of Allowance mailed Sep. 6, 2002", 5 pgs.

(Continued)

*Primary Examiner*—George Manuel
(74) *Attorney, Agent, or Firm*—Schwegman, Lundberg & Woessner, P.A.

(57) ABSTRACT

A cardiac rhythm management (CRM) system includes an implantable cardioverter defibrillator (ICD) and an external system. The ICD detects a tachyarrhythmia episode and classifies the detected tachyarrhythmia episode using none, one, or more of detection enhancements selected according to a selection command including a classification mode. The detection enhancements are each an algorithm for detecting and analyzing one or more indications of a type of the detected tachyarrhythmia episode. The external system allows a user to select the classification mode from a plurality of available classification modes each using none, one, or more of the detection enhancements.

20 Claims, 5 Drawing Sheets

U.S. PATENT DOCUMENTS

| | | | |
|---|---|---|---|
| 5,766,225 | A | 6/1998 | Kramm |
| 5,891,178 | A | 4/1999 | Mann et al. |
| 5,978,707 | A | 11/1999 | Krig et al. |
| 6,088,618 | A | 7/2000 | Kerver |
| 6,151,524 | A | 11/2000 | Krig et al. |
| 6,240,317 | B1 | 5/2001 | Villaseca et al. |
| 6,289,248 | B1 | 9/2001 | Conley et al. |
| 6,308,095 | B1 | 10/2001 | Hsu et al. |
| 6,493,579 | B1 | 12/2002 | Gilkerson et al. |
| 6,522,925 | B1 | 2/2003 | Gilkerson et al. |
| 6,708,058 | B2 | 3/2004 | Kim et al. |
| 7,010,349 | B2 | 3/2006 | Conley et al. |
| 7,113,824 | B2 | 9/2006 | Krig et al. |
| 7,212,849 | B2 | 5/2007 | Zhang et al. |
| 7,522,956 | B2 | 4/2009 | Krig et al. |
| 7,532,931 | B2 | 5/2009 | Gilkerson et al. |
| 7,606,620 | B2 | 10/2009 | Gilkerson et al. |
| 2004/0116982 | A1 | 6/2004 | Conley et al. |
| 2005/0038480 | A1 | 2/2005 | Ding |
| 2005/0149125 | A1* | 7/2005 | Kim et al. ............... 607/5 |
| 2005/0149135 | A1 | 7/2005 | Krig et al. |
| 2006/0095083 | A1 | 5/2006 | Zhang et al. |
| 2006/0167520 | A1 | 7/2006 | Gilkerson et al. |
| 2006/0195147 | A1 | 8/2006 | Gilkerson et al. |
| 2006/0217621 | A1 | 9/2006 | Kim et al. |
| 2009/0005826 | A1* | 1/2009 | Li ............................ 607/5 |
| 2009/0099616 | A1 | 4/2009 | Li et al. |
| 2010/0023075 | A1 | 1/2010 | Gilkerson et al. |

FOREIGN PATENT DOCUMENTS

| | | | |
|---|---|---|---|
| EP | 0401962 | A2 | 12/1990 |
| EP | 0597459 | A2 | 5/1994 |
| EP | 0617980 | A2 | 10/1994 |
| EP | 744190 | A2 | 11/1996 |
| EP | 0748638 | A2 | 12/1996 |
| WO | WO-93/02746 | A1 | 2/1993 |
| WO | WO-2006/039694 | | 4/2006 |
| WO | WO-2009/082422 | A1 | 7/2009 |

OTHER PUBLICATIONS

"U.S. Appl. No. 10/339,926, Non-Final Office Action mailed Nov. 4, 2005", 6 pgs.

"U.S. Appl. No. 11/379,742 Advisory Action mailed Jun. 4, 2010", 3 pgs.

"U.S. Appl. No. 11/379,742, Final Office Action mailed Apr. 1, 2010", 6 pgs.

"U.S. Appl. No. 11/379,742, Preliminary Amendment filed Jun. 8, 2006", 3 pgs.

"U.S. Appl. No. 11/379,742, Response filed May 27, 2010 to Final Office Action mailed Apr. 11, 2010", 11 pgs.

"U.S. Appl. No. 11/379,742, Response filed Dec. 17, 2009 to Non Final Office Action mailed Sep. 24, 2009", 8 pgs.

"U.S. Appl. No. 09/378,029, Non-Final Office Action mailed Mar. 28, 2001", 4 pgs.

"U.S. Appl. No. 09/378,029, Notice of Allowance mailed Apr. 18, 2002", 5 pgs.

"U.S. Appl. No. 09/378,029, Notice of Allowance mailed Aug. 27, 2001", 3 pgs.

"U.S. Appl. No. 09/378,029, Response filed Jun. 28, 2001 to Non-Final Office Action mailed Mar. 28, 2001", 6 pgs.

"U.S. Appl. No. 09/378,029, Supplemental Notice of Allowability mailed Sep. 4, 2002", 2 pgs.

"U.S. Appl. No. 10/025,958, Non-Final Office Action mailed Jan. 8, 2008", 10 pgs.

"U.S. Appl. No. 10/025,958, Notice of Allowance mailed Jan. 2, 2009", 5 pgs.

"U.S. Appl. No. 10/025,958, Response filed Oct. 30, 2007 to Final Office Action mailed Oct. 15, 2007", 17 pgs.

"U.S. Appl. No. 10/025,958, Response filed Dec. 3, 2008 to Final Office Action mailed Sep. 3, 2008", 18 pgs.

"U.S. Appl. No. No. 10/025,958, Final Office Action mailed Oct. 15, 2007", 12 pgs.

"U.S. Appl. No. 10/025,958, Final Office Action mailed Sep. 3, 2008", 11 pgs.

"U.S. Appl. No. 10/025,958, Advisory Action mailed Apr. 8, 2005", 3 pgs.

"U.S. Appl. No. 10/025,958, Amendment and Response filed Sep. 27, 2004 to Non-Final Office Action mailed Jun. 25, 2004", 10 pgs.

"U.S. Appl. No. 10/025,958, Amendment and Response filed Dec. 14, 2005 to Office Actions mailed Aug. 22, 2005 and Sep. 14, 2005", 12 pgs.

"U.S. Appl. No. 10/025,958, Examiner-Initiated interview Summary mailed Jan. 2, 2009", 1 pg.

"U.S. Appl. No. 10/025,958, Final Office Action mailed Dec. 22, 2004", 6 pgs.

"U.S. Appl. No. 10/025,958, Interview Summary mailed Dec. 3, 2008", 2 pgs.

"U.S. Appl. No. 10/025,958, Non-Final Office Action mailed Mar. 26, 2007", 10 pgs.

"U.S. Appl. No. 10/025,958, Non-Final Office Action mailed Jun. 25, 2004", 6 pgs.

"U.S. Appl. No. 10/025,958, Non-Final Office Action mailed Aug. 22, 2005", 5 pgs.

"U.S. Appl. No. 10/025,958, Non-Final Office Action mailed Sep. 12, 2006", 5 pgs.

"U.S. Appl. No. 10/025,958, Notice of Allowance mailed Feb. 2, 2006", 7 pgs.

"U.S. Appl. No. 10/025,958, Preliminary Amendment mailed May 28, 2002", 8 pgs.

"U.S. Appl. No. 10/025,958, Response and Supplemental Preliminary Amendment filed Apr. 12, 2004 to Restriction Requirement mailed Mar. 24, 2004", 9 pgs.

"U.S. Appl. No. 10/025,958, Response filed Mar. 11, 2005 to Final Office Action mailed Dec. 22, 2004", 13 pgs.

"U.S. Appl. No. 10/025,958, Response filed May 8, 2008 to Non-Final Office Action mailed Jan. 8, 2008", 15 pgs.

"U.S. Appl. No. 10/025,958, Response filed Jul. 26, 2007 to Non-Final Office Action mailed Mar. 26, 2007", 14 pgs.

"U.S. Appl. No. 10/025,958, Response filed Dec. 12, 2006 to Non-Final Office Action mailed Sep. 12, 2006", 12 pgs.

"U.S. Appl. No. 10/025,958, Restriction Requirement mailed Mar. 24, 2004", 5 pgs.

"U.S. Appl. No. 10/025,958, Supplemental Office Action mailed Sep. 14, 2005", 6 pgs.

"U.S. Appl. No. 11/369,142, Response filed Feb. 24, 2009 to Non-Final Office Action mailed Nov. 28, 2008", 8 pgs.

"U.S. Appl. No. 11/369,142, Non-Final Office Action mailed Nov. 28, 2008", 4 pgs.

"U.S. Appl. No. 11/369,142, Notice of Allowance mailed Jun. 9, 2009", 4 pgs.

"U.S. Appl. No. 11/379,742, Non-Final Office Action mailed Sep. 24, 2009", 8 pgs.

"U.S. Appl. No. 11/379,742, Response filed Jul. 29, 2009 to Restriction Requirement mailed Jun. 29, 2009", 7 pgs.

"U.S. Appl. No. 11/379,742, Restriction Requirement mailed Jun. 29, 2009", 7 pgs.

"International Application Serial No. PCT/US2008/012459, International Search Report mailed May 4, 2009", 4 pgs.

"International Application Serial No. PCT/US2008/012459, Written Opinion mailed May 4, 2009", 7 pgs.

* cited by examiner

ANTI-TACHYARRHYTHMIA SYSTEM WITH SELECTIVELY ACTIVATED DETECTION ENHANCEMENTS

CROSS-REFERENCE TO RELATED APPLICATION(S)

This application claims the benefit of U.S. Provisional Application No. 61/008,156, filed on Dec. 18, 2007, under 35 U.S.C. §119(e), which is hereby incorporated by reference.

TECHNICAL FIELD

This document relates generally to cardiac rhythm management (CRM) systems and particularly to a system performing tachyarrhythmia detection and classification using selectively activated detection enhancements.

BACKGROUND

Tachyarrhythmias are abnormal heart rhythms characterized by a rapid heart rate. Tachyarrhythmia generally includes supraventricular tachyarrhythmia and ventricular tachyarrhythmia. Fibrillation is a form of tachyarrhythmia further characterized by an irregular heart rhythm. In a normal heart, the sinoatrial (SA) node, the heart's predominant natural pacemaker, generates electrical impulses, called action potentials, that propagate through an electrical conduction system to the atria and then to the ventricles of the heart to excite the myocardial tissues. The atria and ventricles contract in the normal atrio-ventricular sequence and synchrony to result in efficient blood-pumping functions indicated by a normal hemodynamic performance. Ventricular tachyarrhythmia occurs when the electrical impulses propagate along a pathologically formed self-sustaining conductive loop within the ventricles or when a biologic pacemaker (focus) in a ventricle usurps control of the heart rate from the SA node. When the atria and the ventricles become dissociated during ventricular tachyarrhythmia, the ventricles may contract before they are properly filled with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Ventricular cardioversion and defibrillation are used to terminate most ventricular tachyarrhythmias, including ventricular tachycardia (VT), and VF. An implantable cardioverter defibrillator (ICD) is a CRM device that delivers cardioversion/defibrillation pulses, each being an electric shock, to terminate a detected tachyarrhythmia episode by depolarizing the entire myocardium simultaneously and rendering it refractory. An ICD typically also delivers another type of electrical therapy for tachyarrhythmia known as anti-tachycardia pacing (ATP). In ATP, the heart is competitively paced in an effort to interrupt the reentrant loop causing the tachyarrhythmia.

In an ICD that includes ATP and cardioversion/defibrillation capabilities, the efficacy of each available anti-tachyarrhythmia therapy depends on, among other things, origin of the tachyarrhythmia. For example, a ventricular anti-tachycardia therapy is generally ineffective in terminating an atrial tachyarrhythmia. Additionally, the delivery of each cardioversion/defibrillation pulse consumes a considerable amount of power and results in patient discomfort owing to the high voltage of the shock pulses. Therefore, for therapy efficacy, device longevity, and patient satisfaction, among other things, there is a need for accurate classification of each detected tachyarrhythmia episode.

SUMMARY

A CRM system includes an ICD and an external system. The ICD detects a tachyarrhythmia episode and classifies the detected tachyarrhythmia episode using none, one, or more of detection enhancements selected according to a selection command including a classification mode. The detection enhancements are each an algorithm for detecting and analyzing one or more indications of a type of the detected tachyarrhythmia episode. The external system allows a user to select the classification mode from a plurality of available classification modes each using none, one, or more of the detection enhancements.

In one embodiment, a user interface of an external system for communicating with an ICD presents a plurality of available classification modes and receives a user selection of a classification mode from the plurality of available classification modes. The available classification modes each specify whether each detection enhancement module of a plurality of detection enhancement modules of the ICD is to be activated or deactivated according to a pre-selected set of none, one, or more of the detection enhancements.

In one embodiment, a CRM system includes an ICD and an external system that is to be communicatively coupled to the ICD. The ICD includes a tachyarrhythmia detector to detect a tachyarrhythmia episode and a tachyarrthythmia classifier to classify the detected tachyarrhythmia episode. The tachyarrthythmia classifier includes a plurality of detection enhancement modules and a selective activator. The detection enhancement modules are each configured to perform one of a plurality of detection enhancements. The selective activator receives a selection command and activates or deactivates each of the detection enhancement modules according to the selection command. The external system includes a user input device and an external controller. The user input device receives a user selection of a classification mode from a plurality of available classification modes. The available classification modes each specify whether each of the detection enhancement modules is to be activated or deactivated according to a pre-selected set of none, one, or more of the detection enhancements. The external controller produces the selection command in response to the user selection.

In one embodiment, a method for operating an ICD is provided. The ICD includes a plurality of detection enhancement modules each performing one of a plurality of detection enhancements. A user selection of a classification mode is received using an external system communicatively coupled to the ICD. The classification mode is selected from a plurality of available classification modes. Each detection enhancement module of the plurality of detection enhancement modules is activated if it is used in the classification mode, and deactivated if it is not used in the classification mode.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
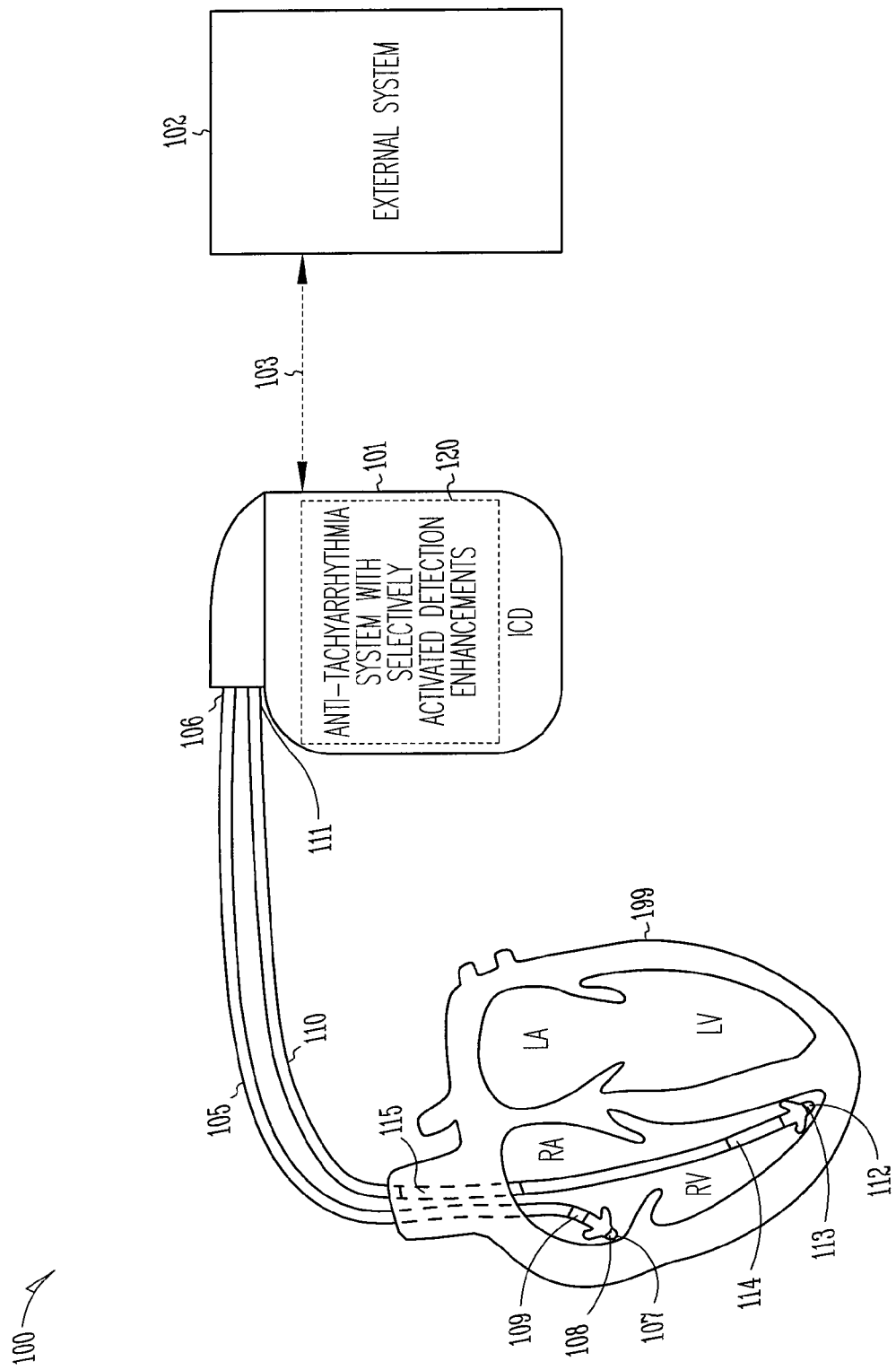
FIG. 1 is an illustration of an embodiment of a CRM system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length (also known as ventricular interval) falls below a tachyarrhythmia threshold interval. The appended claims should be construed to cover such variations.

In this document, a "fast beat" refers to a heart beat having a heart rate that falls into a tachyarrhythmia detection zone, which is typically defined by at least one tachyarrhythmia detection threshold, and a "slow beat" refers to a heart beat having a heart rate that is below the tachyarrhythmia detection zone. In other words, a "fast beat" is a heart beat having a heart rate that is considered tachyarrhythmic, and a "slow beat" is a heart beat having a heart rate that is not considered tachyarrhythmic.

This document discusses, among other things, a CRM system that includes an ICD having a tachyarrhythmia detection and classification circuit that detects tachyarrhythmia episodes using heart rate and includes a plurality of detection enhancements for classifying each detected tachyarrhythmia episode. The detection enhancements are algorithms for detecting and analyzing characteristics of cardiac signals sensed by the ICD for indications of the type, such as the origin, of each detected tachyarrhythmia episode. In the present CRM system, the detection enhancements are grouped into two or more sets each corresponding to a classification mode. Using an external programming device communicating with the ICD, a user, such as a physician or other caregiver, selects one of the classification modes that is believed to be particularly suitable for each patient. Upon detection of a tachyarrhythmia episode using the heart rate, the ICD applies the detection enhancement(s) associated with the selected classification mode to classify each detected tachyarrhythmia episode. When necessary and appropriate according to the result of the classification, the ICD delivers one or more anti-tachyarrhythmia therapies. In one embodiment, the CRM system provides for a plurality of classification modes selectable by the user for the ICD to classify a detected tachyarrhythmia episode as one of VT and SVT and delivers ventricular ATP and/or ventricular cardioversion/defibrillation therapies in response to a VT classification.

FIG. 1 is an illustration of an embodiment of a CRM system 100 and portions of the environment in which CRM system 100 operates. CRM system 100 includes an ICD 101 that is electrically coupled to a heart 199 through leads 105 and 110. An external system 102 communicates with ICD 101 via a telemetry link 103.

ICD 101 is an implantable medical device that performs CRM functions including delivery of cardiac pacing and cardioversion/defibrillation therapies. ICD 101 includes a hermetically sealed can housing an electronic circuit that senses physiological signals and delivers therapeutic electrical pulses. The hermetically sealed can may also function as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is typically a pacing lead that includes a proximal end 106 connected to ICD 101 and a distal end 107 placed in the right atrium (RA) of heart 199. A pacing-sensing electrode 108 is located at distal end 107. Another pacing-sensing electrode 109 is located near distal end 107. Electrodes 108 and 109 are electronically connected to ICD 101 via separate conductors in lead 105 to allow for sensing of the atrial electrogram and/or delivery of atrial pacing pulses. Lead 110 is typically a defibrillation lead that includes a proximal end 111 connected to ICD 101 and a distal end 112 placed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to ICD 101 via separate conductors in lead 110. Electrode 113 and 114 allow for sensing of the ventricular electrogram and/or delivery of ventricular pacing pulses. Electrodes 114 and 115 allow for delivery of ventricular cardioversion/ defibrillation pulses. The functions of these electrodes are discussed above by way of example and not by way of limitation. Other ways of using these electrodes are possible as understood by those of skill in the art.

ICD 101 includes an anti-tachyarrhythmia system 120 that stores a plurality of detection enhancements for selective activation. The detection enhancements are each applied to analyze one or more characteristics of the cardiac signals that are indicative of the origin of an tachyarrhythmia. In one embodiment, anti-tachyarrhythmia system 120 detects a tachyarrhythmia episode using a heart rate detected from a ventricular electrogram. One or more selectively activated detection enhancements are then applied to analyze the ventricular electrogram and an atrial electrogram for indications for VT and SVT. Based on the result provided by each of the selectively activated detection enhancements, anti-tachyarrhythmia system 120 classifies the detected tachyarrhythmia episode as one of VT and SVT. Anti-tachyarrhythmia system 120 is further discussed below, with references to FIGS. 2 and 3.

External system 102 allows for programming of ICD 101 receives signals acquired by ICD 101. The programming of ICD 101 includes the selection of the detection enhancements by the user as further discussed below, with references to FIGS. 4-6. In one embodiment, external system 102 includes a programmer. In another embodiment, external system 102 is a patient management system including an external device in proximity of ICD 101, a remote device in a relatively distant location, and a telecommunication network linking the external device and the remote device. The patient management system provides for access to ICD 101 from a remote location, such as for monitoring patient status and/or adjusting therapies. In one embodiment, telemetry link 103 is an inductive telemetry link. In an alternative embodiment, telemetry link 103 is a far-field radio-frequency telemetry link. Telemetry link 103 provides for data transmission from ICD 101 to external system 102. This may include, for example, transmitting real-time physiological data acquired by ICD 101, extracting physiological data acquired by and stored in ICD 101, extracting therapy history data stored in ICD 101, and extracting data indicating an operational status of ICD 101 (e.g., battery status and lead impedance). Telemetry link 103 also provides for data transmission from external system 102 to ICD 101. This may include, for example, programming ICD 101 to acquire physiological data, programming ICD 101 to perform at least one self-diagnostic test (such as for a device operational status), programming ICD 101 to run a signal analysis algorithm (such as an algorithm implementing a tachyarrhythmia classification method discussed in this document), and programming ICD 101 to deliver pacing and/or cardioversion/defibrillation therapies.

The circuit of ICD 101, including its various elements discussed in this document, may be implemented using a combination of hardware and software. In various embodiments, each element of ICD 101 discussed in this document may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "comparator" includes, among other things, an electronic circuit comparator constructed to perform the only function of a comparison between two signals or a portion of a general-purpose circuit driven by a code instructing that portion of the general-purpose circuit to perform the comparison between the two signals.

Figure 2:
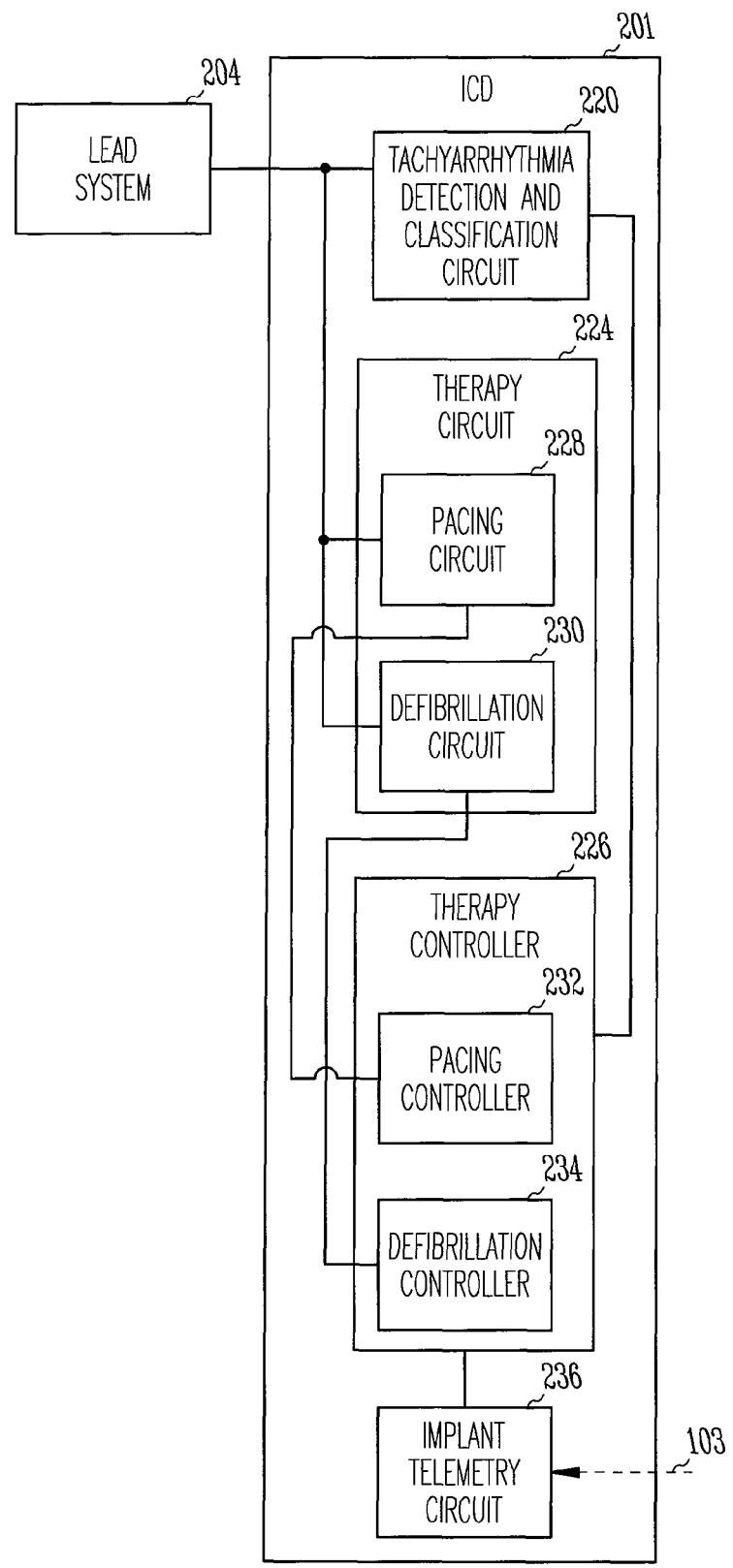
FIG. 2 is a block diagram illustrating an embodiment of an ICD and a lead system of the CRM system.

FIG. 2 is a block diagram illustrating an embodiment of an ICD 201 and a lead system 204. Lead system 204 includes one or more leads such as leads 105 and 110. ICD 201 is a specific embodiment of ICD 101 and includes a tachyarrhythmia detection and classification circuit 220, a therapy circuit 224, a therapy controller 226, and an implant telemetry circuit 236. Tachyarrhythmia detection and classification circuit 220 detects and classifies tachyarrhythmia episode using at least one or more intrinsic electrical cardiac signals sensed using lead system 204. In one embodiment, in addition to one or more cardiac signals, tachyarrhythmia detection and classification circuit 220 uses one or more other physiological signals, such as one or more signals indicative of hemodynamic performance, to detect and classify tachyarrhythmia episode. Therapy circuit 224 includes a pacing circuit 228 to deliver pacing pulses to heart 199 through lead system 204 and a defibrillation circuit 230 to deliver cardioversion/defibrillation pulses to heart 199 through lead system 204. Therapy controller 226 includes a pacing controller 232 to control the delivery of the pacing pulses, including ATP pulses, and a defibrillation controller 234 to control the delivery of the cardioversion/defibrillation pulses. Therapy controller 226 selects one or more of pacing and cardioversion/defibrillation therapies based on the classification of the tachyarrhythmia episode. In one embodiment, an ATP therapy is delivered when a detected tachyarrhythmia is classified as a type of tachyarrhythmia known to be treatable by the ATP therapy. If the ATP therapy fails to terminate the tachyarrhythmia, a cardioversion/defibrillation therapy is delivered. Implant telemetry circuit 236 allows ICD 201 to communicate with external system 102 via telemetry link 103.

Figure 3:
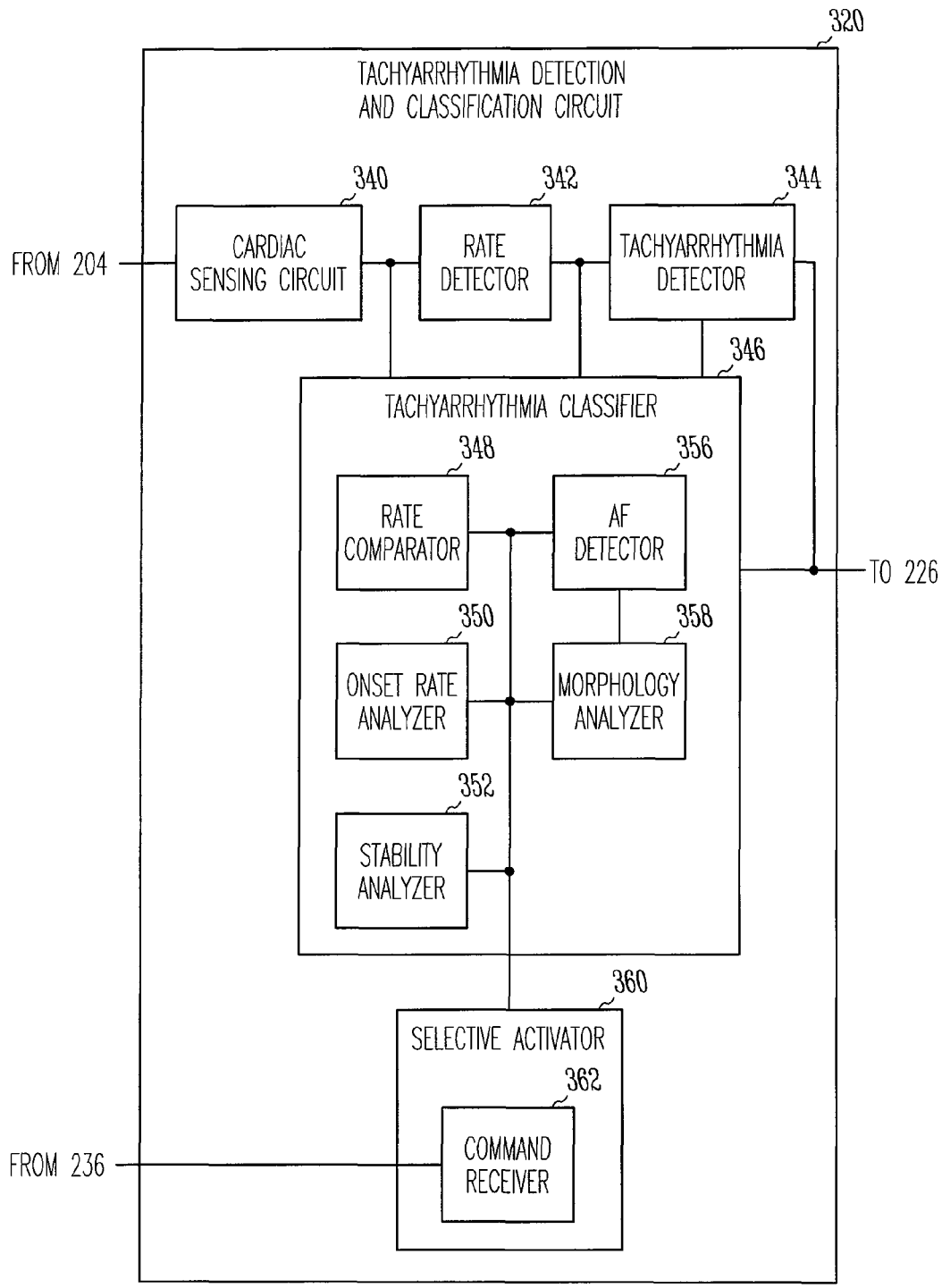
FIG. 3 is a block diagram illustrating an embodiment of a tachyarrhythmia detection and classification circuit of the ICD.

FIG. 3 is a block diagram illustrating an embodiment of a tachyarrhythmia detection and classification circuit 320. Tachyarrhythmia detection and classification circuit 320 is a specific embodiment of tachyarrhythmia detection and classification circuit 220 and includes a cardiac sensing circuit 340, a rate detector 342, a tachyarrhythmia detector 344, a tachyarrhythmia classifier 346, and a selective activator 360.

Cardiac sensing circuit 340 senses one or more cardiac signals, such as one or more electrograms, through lead system 204. In one embodiment, cardiac sensing circuit 340 is electrically coupled to heart 199 through lead system 204 to sense an atrial electrogram and a ventricular electrogram from the heart. The atrial electrogram includes atrial events, also known as P waves, each indicative of an atrial depolarization. The ventricular electrogram includes ventricular events, also known as R waves, each indicative of a ventricular depolarization.

Rate detector 342 detects one or more heart rates from one or more cardiac signals sensed by cardiac sensing circuit 340. In one embodiment, rate detector 342 detects an atrial rate from the atrial electrogram and a ventricular rate from the ventricular electrogram. The atrial rate is the frequency of the atrial events. The ventricular rate is the frequency of the ventricular events. In one embodiment, the atrial and ventricular rates are each expressed in beats per minute (bpm), i.e., number of detected atrial or ventricular depolarizations per minute.

Tachyarrhythmia detector 344 detects a tachyarrhythmia episode. In one embodiment, a tachyarrhythmia is detected when the ventricular rate exceeds a predetermined tachyarrhythmia threshold rate. In one embodiment, tachyarrhythmia detector 344 detects tachyarrhythmia by determining whether the ventricular rate is within one of a plurality of tachyarrhythmia rate zones each including a predetermined threshold rate. In a specific embodiment, the plurality of tachyarrhythmia rate zones includes a VF rate zone with a VF threshold rate programmable between 130 and 250 bpm, a fast VT rate zone with a fast VT threshold rate programmable between 110 and 210 bpm, and a slow VT rate zone with a slow VT threshold rate programmable between 90 and 200 bpm.

Tachyarrhythmia classifier 346 classifies each tachyarrhythmia detected by tachyarrhythmia detector 344. Examples of classification of tachyarrhythmia made by tachyarrhythmia classifier 346 include ventricular fibrillation (VF), ventricular tachycardia (VT), and supraventricular tachycardia (SVT), which includes atrial fibrillation (AF), atrial flutter (AFL), sinus tachycardia (ST), and atrial tachycardia (AT). An example of such tachyarrhythmia classifier providing for classification of VF, VT, SVT, AF, AFL, ST, and AT is discussed in U.S. Provisional Patent Application Ser. No. 60/978,972, "METHOD AND APPARATUS FOR CONCURRENT ATRIO-VENTRICULAR ANTI-TACHYCARDIA PACING", filed on Oct. 10, 2007, assigned to Cardiac Pacemakers, Inc., which is incorporated herein by reference in its entirety.

In one embodiment, tachyarrhythmia classifier 346 stores a plurality of detection enhancements and includes a plurality of detection enhancement modules each configured perform one of the detection enhancements. In the illustrated embodiment, for example, the detection enhancement modules include a rate comparator 348, an onset rate analyzer 350, a stability analyzer 352, an atrial fibrillation (AF) detector 356, and a morphology analyzer 358. Selective activator 360 includes a command receiver 362 to receive from external system 102 a selection command including the classification mode selected by the user. The classification mode corresponds to a selection of none, one, or more of the detection enhancements. According to the selection, selective activator 360 activates none, one, or more of the detection enhancement modules used in the classification mode, and deactivates none, one, or more of the detection enhancement modules not used in the classification mode.

In one embodiment, in response to the detection of a tachyarrhythmia episode by tachyarrhythmia detector 344, tachyarrhythmia classifier 346 classifies the tachyarrhythmia episode as one of VT and SVT. In one embodiment, a VT classification triggers the delivery of a ventricular anti-tachyarrhythmia therapy including ventricular ATP and/or ventricular cardioversion/defibrillation, and an SVT therapy inhibits the delivery of the ventricular anti-tachyarrhythmia therapy.

Rate comparator 348 compares the atrial rate and the ventricular rate to determine whether the ventricular rate is substantially higher than the atrial rate. VT is indicated by a ventricular rate that is higher than the atrial rate by a predetermined margin. In one embodiment, the predetermined margin is programmable by the user. In one embodiment, the predetermined margin is programmed to about 10 bpm.

Onset rate analyzer 350 produces an onset rate of the detected tachyarrhythmia and determines whether the detected tachyarrhythmia has a gradual onset or a sudden onset by comparing the onset rate to one or more threshold onset rates. The onset rate is a rate of transition of the ventricular rate from a normal sinus rate to a tachyarrhythmic rate when the detected tachyarrhythmia begins. A gradual onset typically indicates a physiological tachyarrhythmia, such as SVT caused by exercise. A sudden onset typically indicates a pathological tachyarrhythmia.

Stability analyzer 352 produces a rate stability parameter indicative of a degree of heart rate variability and determines whether the heart rate is stable by comparing the stability parameter to a stability threshold. An unable ventricular stability is an indication of SVT. In one embodiment, a rate stability parameter is produced as an average difference between consecutive ventricular intervals. Stability analyzer 352 determines whether the ventricular rate is stable by comparing the rate stability parameter to the stability threshold. In one embodiment, the stability threshold is programmed by the user. In one embodiment, the stability threshold is programmable between 6 ms and 120 ms.

AF detector 356 compares the atrial rate to an AF rate threshold and declares a detection of AF (a type of SVT) if the atrial rate exceeds the AF rate threshold. In one embodiment, the AF rate threshold is programmed by the user. In one embodiment, the AF rate threshold is programmable between 200 bpm and 400 bpm.

Morphology analyzer 358 analyzes a correlation between a tachyarrhythmic waveform and a template waveform and produces a correlation coefficient representative of that correlation. The tachyarrhythmic waveform includes a segment of a cardiac signal sensed during the detected tachyarrhythmia. In one embodiment, the cardiac signal is the ventricular electrogram. The template waveform is recorded during a known cardiac rhythm such as the normal sinus rhythm (NSR). One example for producing such a correlation coefficient, referred to as a feature correlation coefficient (FCC), is discussed in U.S. Pat. No. 6,708,058, "NORMAL CARDIAC RHYTHM TEMPLATE GENERATION SYSTEM AND METHOD," assigned to Cardiac Pacemakers, Inc., which is hereby incorporated in its entirety. In one embodiment, the detected tachyarrhythmia is considered as "correlated", which indicates SVT, if a correlation coefficient exceeds a correlation threshold.

Figure 4:
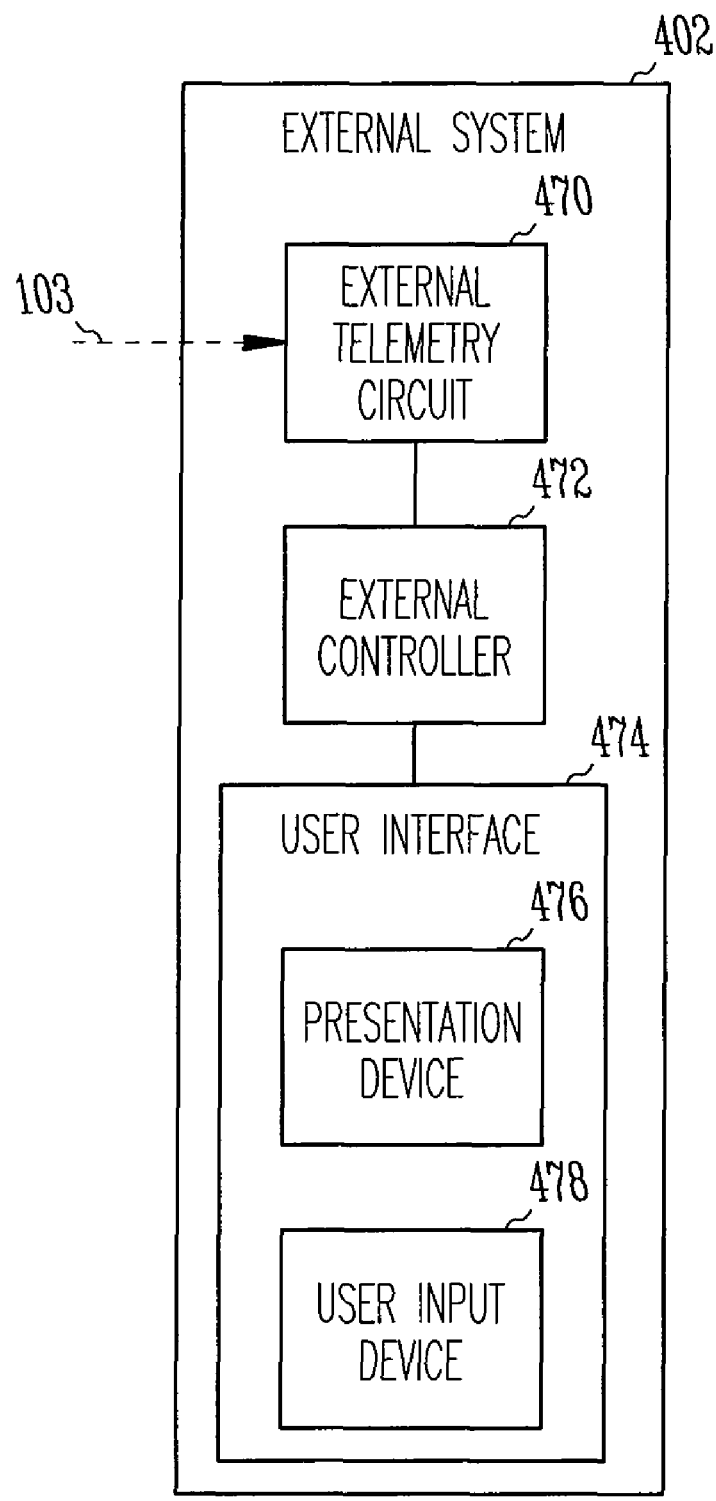
FIG. 4 is a block diagram illustrating an embodiment of an external system of the CRM system.

FIG. 4 is a block diagram illustrating an embodiment of an external system 402. External system 402 is a specific embodiment of external system 102 and includes an external telemetry circuit 470, an external controller 472, and a user interface 474. External telemetry circuit 470 allows external system 402 to communicate with ICD 101 via telemetry link 103. External controller 472 controls the operations of external system 402, including the programming of ICD 101. User interface 474 allows the user to interact with the CRM system, including programming of ICD 101 and monitoring operation status of ICD 101 and condition of the patient in whom ICD 101 is implanted. In the illustrated embodiment, user interface 474 includes a presentation device 476 and a user input device 478. To allow the user to select the classification mode, for example, presentation device 476 presents a plurality of available classification modes, and user input device 478 receives the user's selection of one classification mode of the plurality of available classification modes. In one embodiment, an interactive screen functions as part of both presentation device 476 and user input device 478. After receiving the user selection, external controller 472 produces the selection command including the selected classification mode and programs ICD 101 by transmitting the selection command to ICD 101 via telemetry link 103.

Figure 5:
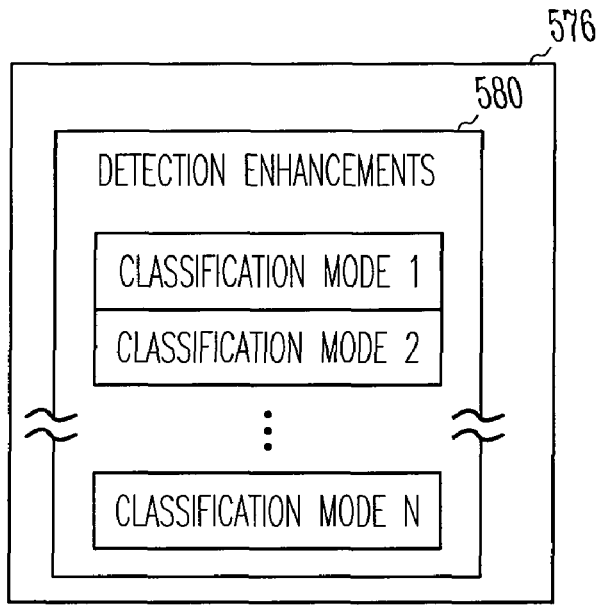
FIG. 5 is an illustration of an embodiment of portions of a screen of a user interface of the external system.

FIG. 5 is an illustration of an embodiment of portions of a screen 576. Screen 576 is a specific embodiment of presentation device 476 and displays a detection enhancements field 580. In the illustrated embodiment, detection enhancements field 580 includes N available classification modes labeled as Classification Mode 1, Classification Mode 2, . . . Classification Mode N. Each of Classification Modes 1 to N includes a selection of none, one, or more of the detection enhancements available in ICD 101. The user selects one of the classification modes by, for example, clicking on the selected classification mode. Examples of the detection enhancements include, but are not limited to, the detection enhancement performed by rate comparator 348 (referred to as V>A), the detection enhancement performed by onset rate analyzer 350 (referred to as Onset), the detection enhancement performed by stability analyzer 352 (referred to as Stability), the detection enhancement performed by AF detector 356 (referred to as AFIB), the detection enhancement performed by morphology analyzer 358 (referred to as Morphology). In a specific embodiment, detection enhancements field 580 includes three available classification modes. Classification Mode 1 uses none of the detection enhancements. Each detected tachyarrhythmia is considered VT, for example, such as when classification is found unreliable for various reasons. Classification Mode 2 (also referred to as One Button Detection Enhancement, or OBDE, by the CRM division of Boston Scientific Corporation, Saint Paul, Minn.) can include V>A, Onset, Stability, and AFIB. Classification Mode 3 (also referred to as RhythmID™ by the CRM division of Boston Scientific Corporation, Saint Paul, Minn.) can include V>A, Stability, AFIB, and Morphology. Because performance of each detection enhancement varies from patient to patient, the user selectivity of the detection enhancement as discussed in this document allows the user to improve performance of tachyarrhythmia detection and classification when needed.

Figure 6:
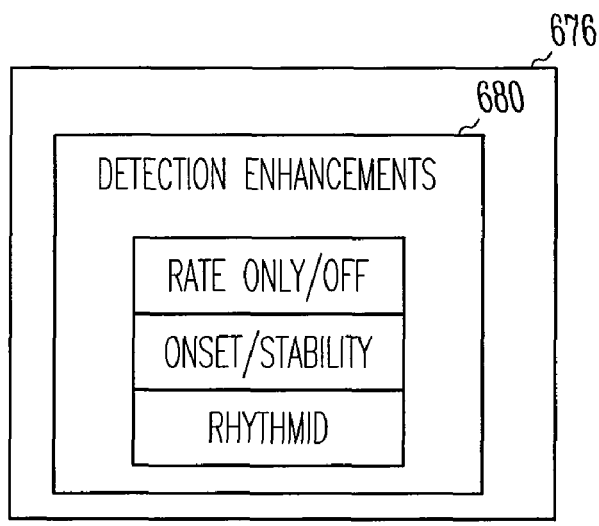
FIG. 6 is an illustration of another embodiment of portions of a screen of a user interface of the external system.

FIG. 6 is an illustration of an embodiment of portions of a screen 676. Screen 576 is a specific embodiment of presentation device 476 and displays a detection enhancement field 680, which illustrates different ways of displaying the user selectable classification modes. In various embodiments, each classification mode is labeled in a way that is easy for the potential users to understand and remember.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An external system for communicating with an implantable cardioverter defibrillator (ICD), the ICD having a plurality of detection enhancement modules configured to perform detection enhancements being algorithms for detecting and analyzing indications of type of tachyarrhythmia, the external system comprising:
   a user interface configured to present a plurality of available classification modes and receive a user selection of a classification mode from the plurality of available classification modes, the available classification modes each specifying whether each detection enhancement module of the plurality of detection enhancement modules, including a morphology analyzer configured to analyze a correlation between a tachyarrhythmic waveform of a cardiac signal sensed during a detected tachyarrhythmia episode and a template waveform, is to be activated or deactivated according to a pre-selected set of none, one, or more of the detection enhancements.

2. The external system of claim 1, wherein the user interface is configured to allow the user selection of a first classification mode according to which none of the detection enhancement modules is to be activated.

3. The external system of claim 1, wherein the user interface is configured to present the plurality of available classification modes each specifying whether each of a rate comparator, an onset rate analyzer, a stability analyzer, an atrial fibrillation (AF) detector, and the morphology analyzer is to be activated or deactivated, the rate comparator configured to determine whether a ventricular rate is substantially higher than an atrial rate, the onset rate analyzer configured to determine whether a detected tachyarrhythmia episode has a gradual onset or a sudden onset as indicated by the ventricular rate, the stability analyzer configured to determine whether the ventricular rate is stable, the atrial AF detector configured to detect AF using the atrial rate.

4. The external system of claim 3, wherein the user interface is configured to allow the user selection of a second classification mode according to which the rate comparator, the onset rate analyzer, the stability analyzer, and the AF detector are to be activated, and the morphology analyzer is to be deactivated.

5. The external system of claim 3, wherein the user interface is configured to allow the user selection of a third classification mode according to which the rate comparator, the stability analyzer, the AF detector, and the morphology analyzer are activated, and the onset rate analyzer is deactivated.

6. The external system of claim 3, wherein the user interface is configured to allow the user selection of one of:
   a first classification mode according to which none of the detection enhancement modules is activated;
   a second classification mode according to which the rate comparator, the onset rate analyzer, the stability analyzer, and the AF detector are activated, and the morphology analyzer is deactivated; and
   a third classification mode according to which the rate comparator, the stability analyzer, the AF detector, and the morphology analyzer are activated, and the onset rate analyzer is deactivated.

7. A cardiac rhythm management system, comprising:
   an implantable cardioverter defibrillator (ICD) including:
      a tachyarrhythmia detector configured to detect a tachyarrhythmia episode; and
      a tachyarrhythmia classifier coupled to the tachyarrhythmia detector and configured to classify the detected tachyarrhythmia episode, the tachyarrhythmia classifier including:
         a plurality of detection enhancement modules each configured to perform one of a plurality of detection enhancements each being an algorithm for detecting and analyzing one or more indications of a type of the detected tachyarrhythmia episode, the plurality of detection enhancement modules including a morphology analyzer configured to analyze a correlation between a tachyarrhythmic waveform of a cardiac signal sensed during the detected tachyarrhythmia episode and a template waveform; and
         a selective activator configured to receive a selection command and activate or deactivate each detection enhancement module of the plurality of detection enhancement modules according to the selection command; and an external system configured to be communicatively coupled to the ICD, the external system including:

a user input device configured to receive a user selection of a classification mode from a plurality of available classification modes each specifying whether each detection enhancement module of the plurality of detection enhancement modules is to be activated or deactivated according to a pre-selected set of none, one, or more of the detection enhancements; and an external controller configured to produce the selection command in response to the user selection.

8. The system of claim 7, wherein the ICD comprises:

a cardiac sensing circuit configured to sense an atrial electrogram and a ventricular electrogram; and a rate detector configured to detect an atrial rate from the atrial electrogram and a ventricular rate from the ventricular electrogram, and wherein the tachyarrhythmia detector is configured to detect the tachyarrhythmia episode using at least the ventricular rate.

9. The system of claim 8, wherein the plurality of detection enhancement modules comprises the morphology analyzer and one or more of:

a rate comparator configured to determine whether the ventricular rate is substantially higher than the atrial rate;

an onset rate analyzer configured to determine whether the detected tachyarrhythmia episode has a gradual onset or a sudden onset as indicated by the ventricular rate;

a stability analyzer configured to determine whether the ventricular rate is stable; and an atrial fibrillation (AF) detector configured to detect AF using the atrial rate.

10. The system of claim 9, wherein the user input device is configured to allow the user selection of a first classification mode according to which none of the detection enhancement modules is activated.

11. The system of claim 9, wherein the plurality of detection enhancement modules comprises at least the rate comparator, the onset rate analyzer, the stability analyzer, and the AF detector, and wherein the user input device is configured to allow the user selection of a second classification mode according to which the rate comparator, the onset rate analyzer, the stability analyzer, and the AF detector are activated.

12. The system of claim 9, wherein the plurality of detection enhancement modules comprises at least the rate comparator, the stability analyzer, the AF detector, and the morphology analyzer, and wherein the user input device is configured to allow the user selection of a third classification mode according to which the rate comparator, the stability analyzer, the AF detector, and the morphology analyzer are activated.

13. The system of claim 9, wherein the plurality of detection enhancement modules comprises the rate comparator, the onset rate analyzer, the stability analyzer, the AF detector, and the morphology analyzer, wherein the user input device is configured to allow the user selection of one of:

a first classification mode according to which none of the detection enhancement modules is activated;

a second classification mode according to which the rate comparator, the onset rate analyzer, the stability analyzer, and the AF detector are activated, and the morphology analyzer is deactivated; and a third classification mode according to which the rate comparator, the stability analyzer, the AF detector, and the morphology analyzer are activated, and the onset rate analyzer is deactivated.

14. A method for operating an implantable cardioverter defibrillator (ICD), the method comprising:

receiving a user selection of a classification mode from a plurality of available classification modes using an external system communicatively coupled to the ICD;

producing a selection command in response to the user selection;

activating each used detection enhancement module of a plurality of detection enhancement modules according to the selection command, the plurality of detection enhancement modules including a morphology analyzer configured to analyze a correlation between a tachyarrhythmic waveform of a cardiac signal sensed during a detected tachyarrhythmia episode and a template waveform, the each used detection enhancement module being a detection enhancement module used in the classification mode; and deactivating each unused detection enhancement module of the plurality of detection enhancement modules according to the selection command, the each unused detection enhancement module being a detection enhancement module not used in the classification mode, wherein the plurality of detection enhancement modules are in the ICD and each configured to perform one of a plurality of detection enhancements each being an algorithm for detecting and analyzing one or more indications of a type of the detected tachyarrhythmia episode.

15. The method of claim 14, comprising:

sensing an atrial electrogram and a ventricular electrogram;

detecting an atrial rate from the atrial electrogram;

detecting a ventricular rate from the ventricular electrogram; and detecting the tachyarrhythmia episode using at least the ventricular rate.

16. The method of claim 15, wherein activating the each used detection enhancement module of the plurality of detection enhancement modules comprises activating none, one, or more of:

a rate comparator configured to determine whether the ventricular rate is substantially higher than the atrial rate;

an onset rate analyzer configured to determine whether the detected tachyarrhythmia episode has a gradual onset or a sudden onset as indicated by the ventricular rate;

a stability analyzer configured to determine whether the ventricular rate is stable;

an atrial fibrillation (AF) detector configured to detect AF using the atrial rate; and the morphology analyzer.

17. The method of claim 16, comprising providing a first classification mode of the plurality of available classification modes for the user selection, the first classification mode using none of the detection enhancement modules.

18. The method of claim 16, comprising providing a second classification mode of the plurality of available classification modes for the user selection, wherein the rate comparator, the onset rate analyzer, the stability analyzer, and the AF detector are used in the second classification mode, and the morphology analyzer is not used in the second classification mode.

19. The method of claim 16, comprising providing a third classification mode of the plurality of available classification modes for the user selection, wherein the rate comparator, the stability analyzer, the AF detector, and the morphology analyzer are used in the third classification mode, and the onset rate analyzer is not used in the third classification mode.

20. The method of claim 16, comprising providing first, second, and third classification modes of the plurality of available classification modes for the user selection, wherein:
- none of the detection enhancement modules is used in the first classification mode;
- the rate comparator, the onset rate analyzer, the stability analyzer, and the AF detector are used, and the morphology analyzer is not used, in the second classification mode; and
- the rate comparator, the stability analyzer, the AF detector, and the morphology analyzer are used, and the onset rate analyzer is not used, in the third classification mode.

* * * * *

UNITED STATES PATENT AND TRADEMARK OFFICE
CERTIFICATE OF CORRECTION

PATENT NO. : 7,840,265 B2 Page 1 of 1
APPLICATION NO. : 12/264771
DATED : November 23, 2010
INVENTOR(S) : David L. Perschbacher et al.

It is certified that error appears in the above-identified patent and that said Letters Patent is hereby corrected as shown below:

In column 10, line 50, in Claim 7, delete "tachyarrthythmia" and insert --tachyarrhythmia--, therefor.

Signed and Sealed this
First Day of March, 2011

David J. Kappos
*Director of the United States Patent and Trademark Office*